United States Patent [19]
Thacker

[11] Patent Number: 5,968,515
[45] Date of Patent: Oct. 19, 1999

[54] METHODS FOR THE QUANTITATIVE ANALYSIS OF ORGANIC COMPOUNDS

[75] Inventor: James D. Thacker, Manassas, Va.

[73] Assignee: Thaco Research, Ltd., Chantilly, Va.

[21] Appl. No.: 08/826,502

[22] Filed: Apr. 3, 1997

Related U.S. Application Data

[62] Division of application No. 08/671,754, Jun. 28, 1996, Pat. No. 5,780,243.

[51] Int. Cl.$^6$ .................................................... A61K 39/385
[52] U.S. Cl. ........................ 424/193.1; 530/403; 514/54; 514/59
[58] Field of Search ............................ 530/403; 436/518, 436/815; 514/4, 54, 57, 59; 424/193.1

[56] References Cited

PUBLICATIONS

Brunswick et al., Specific Radiommunoassay of Amitriptyline and Nortriptyline. British Journal of Clinical Pharmacology 7:343–348, 1979.
Campbell et al., Detection and Quantitation of Chloramphenicol by Competitive Enzyme–Linked Immunoassay, Antimicrobial Agents and Chemotherapy 25(2): 205–211, 1984.
Erlanger, The Preparation of Antigenic Hapten–Carrier Conjugates: A Survey, Methods in Enzymology, vol. 70, pp. 85–104, 1980.
Tanaka et al., Easy Enzyme–LInked Immunosorbent Assay for Spectinomycin in Chicken PlaIsma, Journal of AOAC International 79(2):426–430, 1996.

*Primary Examiner*—Donna C. Wortman
*Attorney, Agent, or Firm*—Baker & Botts

[57] ABSTRACT

The invention comprises a low temperature method for the in situ derivatization and coupling of thermally and hydrolytically labile organic compounds such as spectinomycin to immunogenic carrier substances. The compound coupled to the immunogenic carrier is utilized to produce antibodies selective for the organic compound. Such methods allow for the quantitative analysis of the target organic compound and may be competitive or non-competitive immunoassays in which the dose response is directly or indirectly proportional to the concentration of spectinomycin-related substances. Such assays may be used to detect the presence of or to quantitate the amount of the organic compound in a complex and varied immunological background such as a sample of a biomass material. Detection of organic compound in the sample occurs through binding to a specific antibody. Amplification of that antibody-antigen response to increase the level of detection can be accomplished with a variety of markers producing either a fluorescent, ultraviolet, visible, chemiluminescent, gravimetric, amperometric, voltametric, or radioactive response.

14 Claims, 3 Drawing Sheets

FIGURE 1

NHS

Thiadone

METHODS FOR THE QUANTITATIVE ANALYSIS OF ORGANIC COMPOUNDS

This application is a Divisional of application Ser. No. 08/671,754, filed Jun. 28, 1996, now U.S. Pat. No. 5,780,243, entitled METHODS FOR THE QUANTITATIVE ANALYSIS OF ORGANIC COMPOUNDS.

BACKGROUND OF THE INVENTION

1. Field of the Invention

This invention relates to methods for chemically modifying organic compounds to form haptens chemically bonded to immunogenic substances. The invention further relates to immunological methods to determine the presence or concentration of organic compounds and, in particular, spectinomycin.

2. Description of the Background

Spectinomycin (decahydro-4a,7,9-trihydroxy-2-methyl-6,8-bis(methylamino)-4H-pyrano[2,3-b][1,4]benzodioxin-4-one) is an aminocyclitol antibiotic isolated from the fermentation broth of *Streptomyces spectabilis* (D. J. Mason et al., Antibiot. Chemotherapy 11:118, 1961; E. M. Bergy et al., Antibiot. Chemotherapy 11:661, 1961). The current standard for analysis is a microbiological assay (Marsh et al., J. Assoc. Offic. Anal. Chem. 50:457, 1967; A. W. Neff et al., J. Assoc. Off. Anal. Chem. 56:834, 1973). Although cumbersome, labor intensive and slow, these methods have served as the benchmark for nearly thirty years and are the basis for the U.S. Pharmacopoeia guidelines as well as the World Health Organization analytical standards. Recently this methodology was modified to incorporate a trifluoroacetic acid extraction step (G. L. Stahl et al., J. Assoc. Off Anal. Chem. 74:471, 1995).

To improve the detectability of any analyte, the analytical paradigm suggests that the analyte can be modified to enhance its detectability, for example, chemical derivatization to introduce a chromaphore onto the analyte. Similarly, the use of a detection device that is more sensitive to the analyte, for example, fluorimetric versus colorimetric analysis will also enhance detectability. In the alternative, removal of interfering substances through the use of chromatographic separations for instance, will enhance the detectability of the analyte.

Spectinomycin represents one of the more challenging analytical problems of detectability due, in part, to the absence of a chromaphore and virtual insolubility of spectinomycin in organic solvents. As such, Spectinomycin represents a broad class of organic compounds being thermally and/or hydrolytically labile and for which improved methods of analysis are desired. To improve the detectability of spectinomycin, several approaches have been attempted over the years. Elrod employed an electrochemical detector after separation of the spectinomycin and spectinomycin-related residues by HPLC (L. Elrod et al., Pharm. Res. 5:664, 1988). Phillips used pulsed amperometric detection after cation exchange chromatography (J. G. Phillips et al., J. Chromatog. 675:123, 1994). Abbay used dynamic headspace gas chromatographic analysis of bulk spectinomycin hydrochloride (G. N. Abbay et al., LC-GC 9:100, 1991). Medina used thin layer chromatography for the semi-quantitative analysis of derivatized aminocyclitols including spectinomycin (M. B. Medina, J. Chrom. 663:127, 1995). Other derivatization strategies, followed by chromatographic analysis, have been employed by us and others. For instance, amine derivatizing agents such as 1-fluoro-2,4-nitrophenyl-5-alanine amide (FDAA or Marfey's Reagent) or 9-fluorenylmethyl chloroformate (Fmoc-Chloride) have been used to derivatize spectinomycin prior to HPLC analysis with either UV or fluorescence detection respectively. Similarly, spectinomycin has been derivatized as the trifluoromethyl ethers, trifluoroacetyl esters, and trimethylsilyl ethers, followed by gas chromatographic analysis and electron capture detection.

Immunochemical methods of analysis address the analytical paradigm in two ways. First, the antibodies themselves are highly specific for the antigen (analyte), and second, either the antigen, the antibody or an antiglobulin may be conjugated to an enzyme that produces an intensely colored or fluorescent product in the presence of the enzyme substrate to enhance the detectability. Various formats for immunochemical assays have been employed in either competitive or non-competitive assays with the detector response being either directly or indirectly proportional to the analyte concentration (J. Clausen, *Immunochemical Techniques for the Identification and Estimation of Macromolecules*, 3rd revised edition, R. H. Burdon and P. H. Knippenberg eds., Elsevier Science Publishers, New York, 1991).

Low molecular weight compounds such as spectinomycin are not typically antigenic and, therefore, such compounds are not capable of eliciting an immune response by themselves. The chemistry of methods utilized to conjugate small molecules to proteins and other immunogenic substances has been extensively described by Clausen as well as by Wong and the references therein (S. S. Wong, *Chemistry of Protein Conjugation and Cross-Linking*, CRC Press, Inc., Boca Raton, 1993). Heterocyclic compounds, including aminocyclitols like spectinomycin, require additional chemical modification prior to conjugation to a protein or other immunogenic substance. The chemistry for the addition of a four-carbon carboxyl spacer arm via condensation with succinic anhydride to form succinyl esters was first described for estrogenic steroids (Tulchinsky et al., J. Clin. Endocrinol. Metab. 33:775, 1971; Wu et al., Steroids 18:91, 1971; Emment et al., Acta Endocrinol. 69:567, 1972). These reactions required several hours of incubation or reflux conditions that would degrade a thermally labile compound such as spectinomycin or would result in multiple products.

Thus, there exists a need for a method of analysis to determine spectinomycin that is at once specific, sensitive, reliable, quantitative and inexpensive to perform. Whereas immunochemical methods of analysis could potentially fulfill these requirements, there also exists a need for a method to convert thermally and hydrolytically labile compounds such as spectinomycin into an immunogen by chemical derivatization at ambient or sub-ambient temperatures and at or near neutral pH conditions with efficient coupling to an immunogenic substance.

SUMMARY OF THE INVENTION

The present invention overcomes the problems and disadvantages associated with current strategies and designs and provides novel methods, antigens and antibodies to quantitatively detect organic compounds.

One embodiment of the invention is directed to a process for the chemical modification of organic compounds to form immunogens. The basic process comprises adding an organic compound containing amine, hydroxyl or sulfhydryl functional groups to a homobifunctional carboxylic cross-linking agent in the presence of a hydroxylimide catalyst to form an adduct with a free carboxyl moiety. The free carboxyl moiety of the adduct is activated with a carbodiimide and a urea group is eliminated by the hydroxylimide catalyst to form an activated ester. The active ester is conjugated to an immunogenic carrier containing a primary amine to form the immunogen having, at least, the immunological specificity of the organic compound and the immunogenicity of the carrier.

Another embodiment of the invention is directed to immunogens prepared by adding organic compounds containing amine, hydroxyl or sulfhydryl functional groups to homobifunctional carboxylic cross-linking agents in the presence of a hydroxylimide catalyst to form an adduct with a free carboxyl moiety, activating the carboxyl moiety with a carbodiimide, removal of a urea group by the hydroxylimide catalyst to form an activated ester and conjugating the activated ester with an immunogenic carrier substance containing a primary amine. Immunogenic substances prepared according to this method, referred to herein as N-hydroxysuccinimide-derived (NHS) immunogens, can be utilized, for example, to generate antibodies or to serve as antigens such as coating antigens in ELISA assays.

Another embodiment of the invention is directed to antibodies that are specifically reactive against NHS immunogens of the invention. Such antibodies may be polyclonal or monoclonal and can be obtained from most any mammalian species or recombinantly synthesized.

Another embodiment of the invention is directed to a process for the quantitation of organic compounds in a sample. The process comprises contacting primary antibodies, prepared against NHS immunogens, with the sample. Primary antibodies of the mixture are contacted to a solid support to which NHS immunogens are attached. Fixed primary antibodies are contacted with secondary antibodies directed against the primary antibody and the amount of organic compound in the sample is determined thusly.

Another embodiment of the invention is directed to a process for quantifying an amount of an organic compound in a sample. The process comprises contacting the sample with antibodies against an NHS immunogen derived from the organic compound, to bind the antibodies to organic compound. Antibodies are subsequently contacted to a coating antigen fixed to a solid support and the amount of fixed antibodies determined. As the process is both rapid and sensitive, a wide variety of samples can be tested and screened for the presence and to determine the concentration of organic compounds such as spectinomycin.

Another embodiment of the invention is directed to processes for quantifying an amount of an organic compound in a sample. The process comprises contacting the sample with antibodies against an NHS immunogen derived from the organic compound wherein the antibodies are conjugated with a detectable marker. Antibodies are subsequently contacted to a coating antigen fixed to a solid support and the amount of fixed antibodies determined.

Another embodiment of the invention is directed to kits for the detection or quantitation of organic compounds in a sample obtained from an immunologically complex background. Such kits may contain NHS immunogen, optionally fixed to a solid support, antibodies reactive against the NHS immunogen or both, and sufficient instruction for an ordinary person to be able to successfully use the kit in the laboratory or in the field.

Other embodiments and advantages of the invention are set forth, in part, in the description which follows and, in part, will be obvious from this description and may be learned from the practice of the invention.

DESCRIPTION OF THE INVENTION

As embodied and broadly described herein, the present invention is directed to methods, antigens and antibodies that can be used to quantitatively detect organic compounds and to kits that comprise such antigens or antibodies.

Conventional techniques for the detection and quantitative analysis of organic compounds in complex backgrounds are cumbersome and labor intensive. Accurate results typically require repetitive measurements which double or triple the already high costs associated with such techniques.

It has been discovered that the yield of succinylated product (hapten) resulting from condensation of succinic anhydride with an organic compound can be significantly improved by the presence of catalytic amounts of N-hydroxysuccinimide added to the derivatization reaction. Use of an N-hydroxysuccinimide as the catalyst is surprising as such an N-hydroximide would not have been expected to successfully catalyze the conjugation reaction under mild conditions and in a short time frame. Consequently, by coupling the succinylated product (hapten) to an immunogenic carrier and using this conjugate (immunogen) to create target-specific antibodies, the organic compound can be accurately and quantitatively detected even at fairly low concentrations and in complex background conditions.

According to this method, the catalyst facilitates formation of an "activated" succinyl ester at reduced temperature, thus minimizing competing side reactions and degradations. Absence of a need to isolate intermediates, owing to the choice of N-hydroxysuccinimide as the initial "activating" catalyst, creates the in situ derivatization process. Choice of succinic anhydride as the derivatizing reagent gives rise to a homobifunctional spacer arm containing a carboxyl terminal end that is activated in the second step for coupling to the immunogenic carrier substance. Condensation of the carboxyl-containing hapten with a substituted carbodiimide forms an acylisourea intermediate that is eliminated by the N-hydroxysuccinimide catalyst to form a second active ester. The hapten, thus activated, may be directly coupled to the immunogenic carrier. As a result of the lower reaction temperature, the choice of reagents and the in situ process described, the overall yield of the desired product is increased.

An object of the present invention is to provide an in situ method for chemical derivatization of thermally and hydrolytically labile organic compounds, such as spectinomycin and other low molecular weight compounds, without degradation to produce an immunogenic substance such that an immune response can be generated in a test animal and antibodies specific to the unmodified parent compound can be collected.

Another object of the invention is to produce antibodies with sufficient selectivity to the antigen yet with little or no cross-reactivity to other unrelated substances.

Another object of the invention is to provide a method for detection and quantitation of the antigen that is at once rapid, specific and highly sensitive.

Production of NHS Immunogens

One embodiment of the invention is directed to a method for the in situ succinylation of a thermally or hydrolytically labile organic compound containing nucleophilic functional groups and conjugation of the succinylate to an immunogenic substance containing amine functional groups. This process relies on succinylation to derivative the organic compound, and an activated ester coupling to conjugate the succinylated hapten to the carrier. The basic method uses a two-stage procedure where an organic compound is derivatized to form an activated hapten in the first stage, followed by coupling the derivatized hapten to a carrier moiety of known immunogenicity in the second stage. Derivatization is carried out in the presence of succinic anhydride and a catalytic amount of N-hydroxysuccinimide and both the derivatization and coupling reactions proceed in situ. Consequently, the resulting conjugate possesses, at least, the immunological specificity of the hapten and the immunogenic strength of the carrier moiety. These immunogens are herein referred to as NHS-derived or simply NHS immunogens.

The presence of the catalyst in a mixture of the substance to be succinylated (target antigen) and succinic anhydride results in significantly greater yield of the desired succinylated product (activated hapten). Significantly means that the yield is at least sufficient to produce a recoverable product.

The mechanism of the reaction for producing the activated hapten is a two-step process. The first step is nucleophilic addition of N-hydroxysuccinimide to succinic anhydride to form the O-succinylsuccinimide activated ester and is probably the rate-limiting step. The second step is the condensation of the activated succinyl ester with a nucleophilic substituent on the target antigen, followed by elimination of N-hydroxysuccinimide to form a succinylated hapten.

Figure 1:
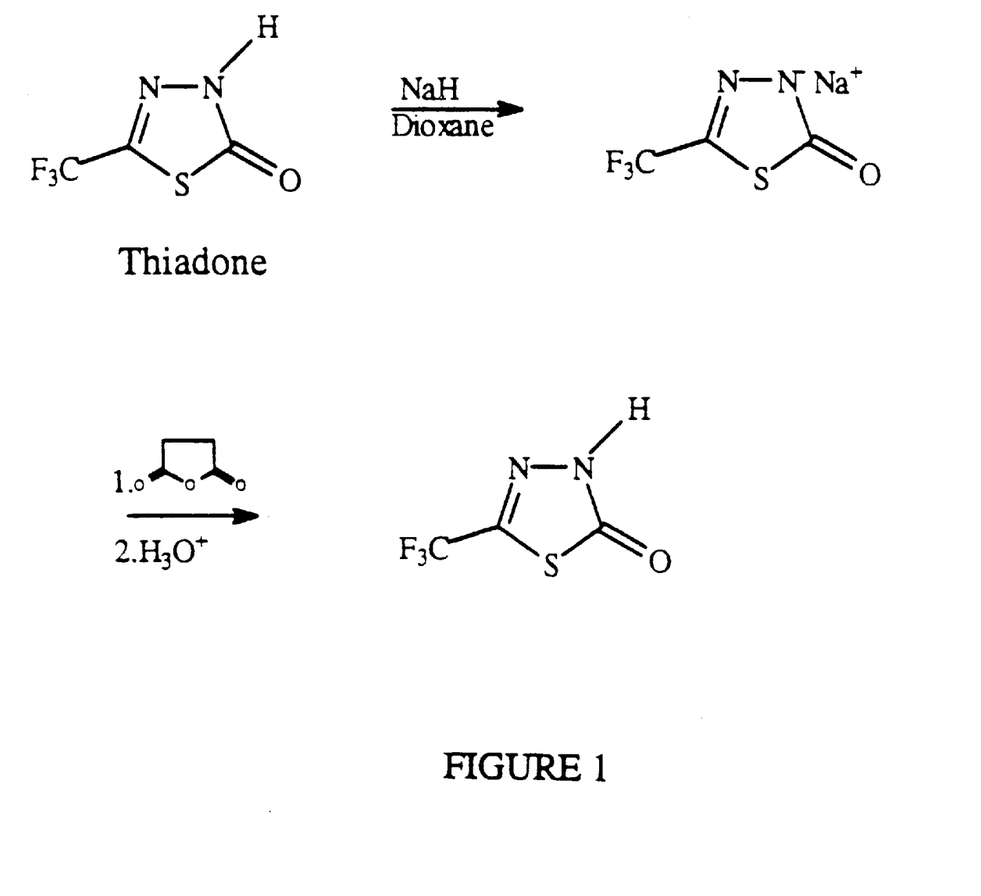
FIG. 1  Chemical preparation of the sodium thiodonyl anion.
Figure 2:
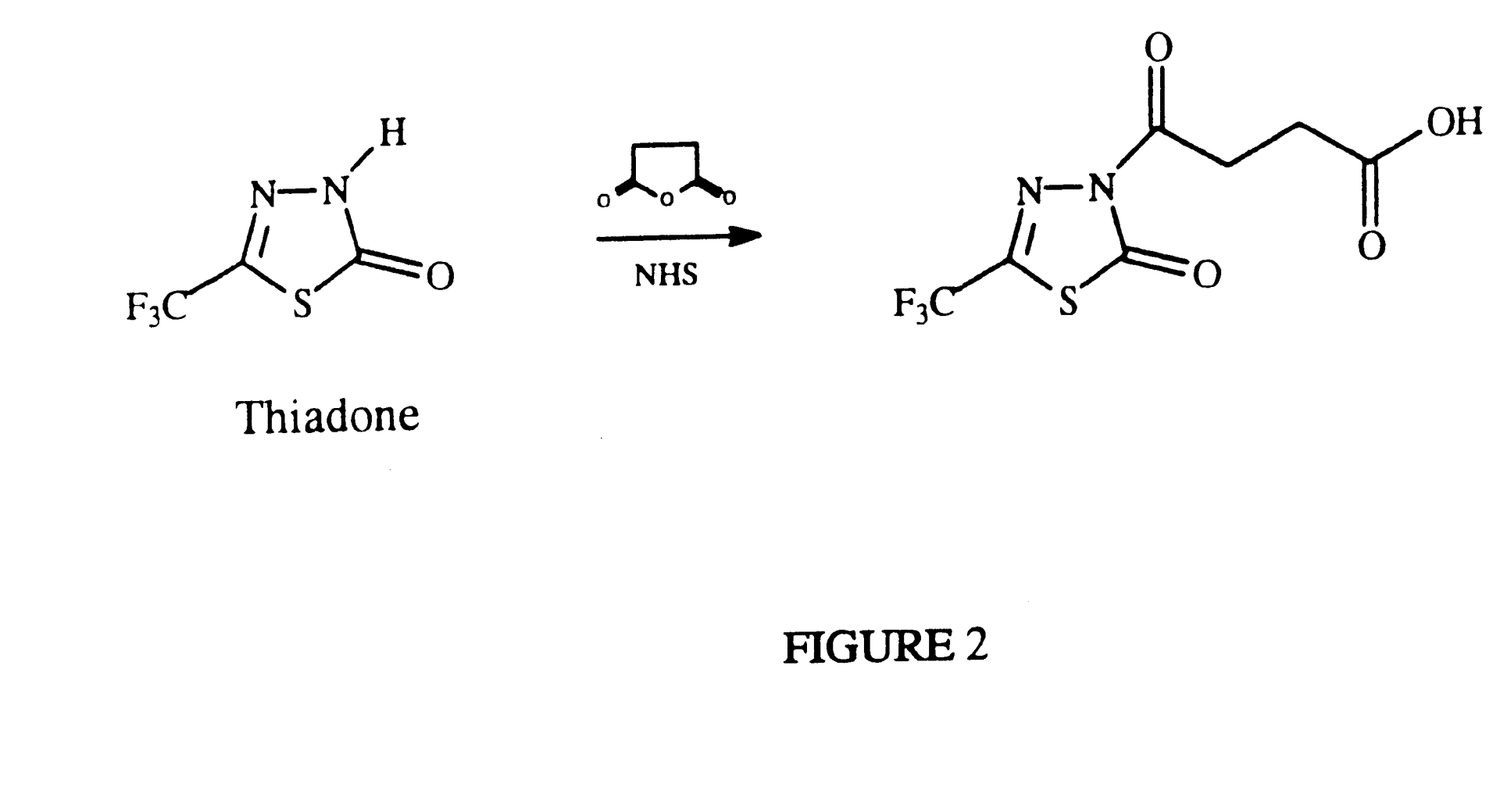
FIG. 2  Chemical preparation of the 3-N-succinylthiadone product.

Empirical evidence indicates that the rate of nucleophilic displacement reactions of the Sn2 type, such as the first step of the process, follows the order $RSH > RNH_2 >> R_2NH >>> ROH$. An anion of 2-oxo-5-(trifluoromethyl)-1,3,4-thiadiazone (Thiadone), prepared from the addition of sodium hydride to a solution of thiadone in anhydrous dioxane, failed to produce succinylthiadone after the addition of succinic anhydride and incubation of the reaction mixture at room temperature (nominally 22° C.) after as much as 24 hours. After work up of the reaction mixture only thiadone was isolated. This reaction sequence is depicted in FIG. 1. In contrast, when thiadone was reacted with an equimolar amount of succinic anhydride in the presence of a catalytic amount of N-hydroxysuccinimide in dimethyl formamide the N-succinylthiadone derivative was isolated in nearly quantitative yield (nearly 100%) after only four hours of incubation at room temperature (about 22° C.). This reaction sequence is depicted in FIG. 2.

The resulting free carboxyl group on the succinylated hapten is available for coupling to an immunogenic carrier. Subsequent coupling of the carboxyl-containing hapten to a protein utilizes the carbodiimide condensation described by Sheehan and Hess, and Khorana (Sheehan and Hess, J. Am. Chem. Soc. 77:1067, 1955; Khorana, Chem. Ind. 1087, 1995). The reaction is a condensation of the hapten carboxyl with a substituted carbodiimide to form an active O-acylisourea intermediate. Nucleophilic substitution with an amine such as the ε-amine of lysine forms the stable amide with elimination of the substituted urea. The poor coupling efficiency of the carbodiimide reaction is improved when N-hydroxysuccinimide is introduced to form the intermediate active N-hydroxysuccinyl ester (Anderson et al., J. Am. Chem. Soc. 86:839, 1964). Gross et al. noted the formation of the bis-N-hydroxysuccinyl ester of β-alanine from the condensation between one mole of N-hydroxysuccinimide and three moles of dicyclohexylcarbodiimide (Gross et al., Tetrahedron 24:6939, 1968). This reaction represents a significant potential for a competing side reaction in coupling reactions using carbodiimide activated carboxyls and N-hydroxysuccinimide displacement. Whereas Wilcheck et al. found this side reaction to be a limitation in their efforts to utilize N-hydroxysuccinimide esters for protein immobilization, the reduced temperatures utilized in the present invention minimizes this competing side reaction (Wilchek et al., Biochemistry 26:2155, 1987).

Whereas other alkyl or aryl carbodiimides are satisfactory carboxyl activators, in a preferred embodiment, the activating reagent is dicyclohexylcarbodiimide, and it is that condensation between dicyclohexylcarbodiimide and the free carboxyl of the succinylated hapten that forms a reactive intermediate O-acylisourea ester which is immediately displaced by the N-hydroxysuccinimide already present from the first step to form a second "activated ester." After removal of the dicyclohexylurea precipitate with centrifugation, the supernatant may be transferred to an aqueous solution of an immunogenic carrier, usually a protein such as keyhole limpet hemocyanin, bovine serum albumin, ovalbumin or the like as well as polysaccharides modified to introduce free amine functional groups, or synthetic polymers such as dextrans, sepharoses, latex or the like. Conjugation to the carrier occurs at about room temperature and is complete in less than about 24 hours, preferably less than about 12 hours and more preferably less than about 6 hours or within about 3 to about 4 hours. Overall yields of conjugated protein are typically greater than about 70%, preferably greater than about 80% and more preferably greater than about 90%, with no or nearly no detectable side reactions or degradations of thermal or hydrolytic labile antigens.

The improved yields and purity resulting when derivatization is carried out in the in situ manner as described herein, arise from the reduced temperatures of the succinylation reaction, owing to the initial formation of an activated succinyl ester. Moreover, the absence of a need to isolate intermediates, owing to the choice of N-hydroxysuccinimide as the initial activating catalyst and succinic anhydride as the derivatizing reagent, creates the in situ derivatization process described in the preferred embodiment of this invention. As a direct result of the in situ process, overall yield of the desired product is substantially increased. Substantially increased means that the resulting amount of product present is such that recovery becomes practical to one of ordinary skill in the art. Preferably, product yield is greater than about 50%, more preferably greater than about 75%, and still more preferably greater than about 90%.

For illustrative purposes, the present invention is described using as an example the succinylation of spectinomycin. However, it is clear to those of ordinary skill in the art that the method is applicable to many different organic compounds. The in situ condensation of spectinomycin with an equimolar amount of succinic anhydride in the presence of catalytic N-hydroxysuccinimide at 4° C. is followed by the subsequent addition of dicyclohexylcarbodiimide, removal of the dicyclohexylurea elimination product and addition of the reaction mixture to an aqueous solution of protein. The choice of an alternative organic compound in which a nucleophile is either present or is added by other chemical derivatization procedures is not limited to spectinomycin or amine functional groups. For example, production of immunogenic conjugates using the derivatization and coupling reactions of this invention has been demonstrated for dihydrospectinomycin, penicillin, ceftiofur, sulfamethazine, chloramphenicol, erythromycin, formazan, bronopol, 2-oxo-5-(trifluoromethyl)-1,3,4-thiadiazone, and an N-derivatized 2-hydroxyacetamide herbicide, FOE 5043. Additional compounds which could be conjugated according to this method can be determined by those of ordinary skill in the art from the practice of the method or knowledge of the claimed properties of the specific compound of interest.

Production of Anti-NHS Immunogen Antibodies

Another embodiment of the invention comprises antibodies that are specifically reactive with NHS immunogens of the invention. Such antibodies may be obtained using most any of the conventional techniques for the generation of antibodies, all of which are well-known to those of ordinary skill in the art (e.g., *Current Protocols in Immunology*, eds. J. E. Coligan et al., John Wiley & Sons, New York, 1996). For example, NHS immunogens, such as described above for spectinomycin, can be injected into an animal to elicit polyclonal antibody production. Purification of the antibodies can be accomplished by selective binding from the serum such as, for example, using a protein A affinity column. This resultant polyclonal antisera may be used directly or may be purified, for example, by affinity absorption using the immunogen coupled to an insoluble support.

Alternatively, monoclonal antibodies specifically immunoreactive with the immunogen may be prepared (Kohler et al., Eur. J. Immunol. 6:611, 1976), using the conjugate as the immunogen or for selection or for both functions. Antibodies may be derived from most any mammalian species such as, for example, mouse, rabbit, goat, monkey or human. These and other methods for preparing antibodies that are specifically immunoreactive with the NHS immunogen are within the ability of those of ordinary skill in the art. Antibodies, either polyclonal or monoclonal may be of the class IgG, IgM IgE, IgD or IgA, and are preferably IgG or IgM. The term antibodies is also intended to include antibody fragments, such as Fab and Fv fragments, recombinant constructs of antibodies such as humanized antibodies or proteins wherein antibody binding regions have been genetically or synthetically introduced.

Another embodiment of the invention is directed to hybridoma cell lines that express antibodies reactive against NHS immunogens of the invention. Such hybridomas can be prepared and maintained according to well-established procedures that are well-known to those of ordinary skill in the art. Cell lines may be stored by cryopreservation or maintained as continuously growing cultures, as desired.

Immunoassays for the Detection of NHS Immunogen

Another embodiment of the invention is directed to methods for the use of antibodies in the determination or quantitation of the organic compound. These methods (e.g. RIA, EIA, ELISA) may be competitive or non-competitive assays with a dose response relationship that is directly or indirectly proportional to the concentration of the organic compound. Such methods provide greater precision and accuracy with improved sensitivity, a greater laboratory throughput and a reduced analytical cost, as compared to conventional methods of analysis.

Immunoassays that can be used include, for example, solid- and liquid-phase ELISA with competitive or non-competitive analysis. Primary and secondary antibodies may be used wherein sample containing organic compound is contacted with primary antibodies (i.e. antibodies prepared against the NHS immunogen which may be monoclonal or polyclonal). Primary antibodies that bind to organic compound can be directly detected by conjugating the primary antibodies with a detectable marker. Alternatively, secondary antibodies may be added to detect either bound or unbound primary antibodies, wherein the secondary antibodies are conjugated to a detectable marker. Detection and quantitation of the amount of marker as compared to controls (e.g. 0% and 100% binding) allows for an accurate determination of the amount of organic compound in the sample. For additional accuracy, the amount of binding could also be compared to a set of control samples containing known, but different amounts of organic compounds (standard curve).

Antibodies prepared against NHS immunogens can be used to detect organic molecules corresponding to the hapten (cross-reactive organic molecules) in tissue sections or extracts of tissues. Antibody binding to tissue sections can be detected by any detection means known in the art such as, for example, a specific radiolabel or stain. A particularly useful stain employs peroxidase, hydrogen peroxide and a chromogenic substance such as aminoethyl carbazole. Peroxidase, a well known enzyme available from many sources, can be coupled to an antibody according to this invention or merely complexed via one or more antibodies to an antibody which specifically binds the hapten-protein conjugate which is cross-reactive with the organic molecule to be detected. Such techniques as well as other chromogenic substances and enzymes are all well known to those of ordinary skill in the art. Radiolabeling of antibodies may also be used to detect antibody binding to sections. Labeled antibodies may be specific for the NHS immunogen or second antibodies immunoreactive with the antibodies of this invention. Again, such techniques are well known to those of ordinary skill in the art.

The precise technique by which an organic molecule cross-reactive with NHS immunogen can be detected in patients can vary widely. Biochemical or immunological techniques can be used which do not employ immunohistochemistry. Solution assay methods, including colorimetric, chemiluminescent or fluorescent immunoassays such as ELISA, sandwich and competitive immunoassays, immuno-diffusion, radioimmunoassay, immunoelectrophoresis, and other techniques, may be used to detect and quantitate an organic molecule cross-reactive with the NHS immunogen by preparing an extract of a tissue sample and assaying the extract.

A cross-reactive organic molecule can be quantitated in a biological fluid, such as serum, plasma, effusions, ascites, urine, cerebrospinal fluid, semen, breast aspirates and fluids of ovarian origin, using any immunoassay means well known to those of ordinary skill in the art. These include such techniques as, for example, a radioimmunoassay, enzyme-linked immuno-adsorbent assay, complement fixation assay, nephelometric assay, immunodiffusion or immuno-electrophoretic assay, and the like. Plasma is preferably anti-coagulated before assay, as is known in the art. Cellular elements and lipid may be removed from fluids by, for example, centrifugation, filtration or selective adsorption to membranes. For dilute fluids, such as urine, protein may be concentrated, for example, by ultra-filtration or salting-out.

Another embodiment of the invention is directed to kits that can be used for the detection, screening and quantitation of the presence or quantitative amount of a specific organic compound in a sample with a complex background of other substances. Kits contain the NHS immunogen or antibodies that specifically react to that immunogen. In a preferred embodiment, the kit comprises NHS immunogen, a solid support, a separate container containing antibodies reactive against the NHS immunogen and instructions for contacting a sample suspected to contain the organic compound to the antibodies and to the solid support. The preferred embodiment further comprises a means for detecting an organic compound that has been bound to the solid support. Organic compounds that can be detected and quantitated with such kits include, for example, spectinomycin. Sample from which organic compounds may be detected include such complex backgrounds as, for example, biomass samples such as soil and plant samples, water samples, samples of tissue and bodily fluids such as blood, and samples of sludge and other solid-waste materials.

For illustrative purposes, the present invention is described using an example of a competitive-type assay in an enzyme-linked immunosorbent (ELISA) format wherein the dose-response relationship is inversely proportional to the concentration of spectinomycin-related residues. However, the scope of the invention is not limited to spectinomycin. Any substance that is either antigenic or can be made antigenic by employing the methods and practices described in the invention. The scope of the invention is also not limited to the antigen-immobilized ELISA format. An antibody-immobilized ELISA format may also be used. The scope of the invention is not limited to utilizing an enzyme-linked antiglobulin to amplify the detection of spectinomycin or spectinomycin residues. The invention also contemplates choice of the antigen-enzyme conjugate or the antibody-enzyme conjugate. The scope of the invention is also not limited to utilizing an enzyme-substrate reaction to amplify the detection of spectinomycin or spectinomycin-related residues. The invention also contemplates choice of either an ultraviolet, fluorescent, visible, radioactive, gravimetric, amperometric, voltametric or magnetic marker. The scope of the invention is not limited to a competitive-type assay as the invention also contemplates choice of a non-competitive assay. The scope of the invention is not limited to a dose-response curve with inverse proportionality as this invention also contemplates choice of an assay that has a directly proportional dose-response relationship.

The following examples are offered to illustrate embodiments of the invention and should not be viewed as limiting the scope of the invention.

EXAMPLES

Example 1

Preparation of Succinylated Antigen and Conjugation to Carrier

Sodium thiodonyl anion was prepared by reaction of thiadone with sodium hydride in anhydrous dioxane (FIG. 1). An equimolar amount of succinic anhydride was added in an hydrous dioxane and the reaction mixture was stirred for 24 hours at nominally 22° C. After quenching the reaction with aqueous HCI the only product to be isolated was thiadone in nearly quantitative yield.

Thiadone, dissolved in dimethylformamide (DMF), and equimolar amount of succinic anhydride also dissolved in DMF, were added to a third solution of N-hydroxysuccinimide in DMF (FIG. 2). After stirring at nominally 22° C. for four hours the 3-N-succinylthiadone product was isolated in nearly quantitative yield.

The keto form of spectinomycin was prepared by dissolving 2 g spectinomycin dihydrochloride pentahydrate in 30 mL cold, deionized water and adding this solution to a cold slurry of 6 mL Amberlite IRA-400 OH in 30 mL deionized water. After stirring for 30 minutes in an ice bath, the resin was poured into a column (1×10 cm) with a fritted glass support and washed with approximately 30 mL deionized water. Final effluent (90 mL) was transferred to a round bottom flask and evaporated in vacuo in a rotary evaporator with the water bath temperature at 55° C. Resulting glassy solid was recrystallized from water and acetone. Resulting crystalline product was dried in a vacuum oven at 60–70° C. overnight.

In a 1-mL ReactiVial™(Pierce Chemical Co.), equal molar amounts (21 mmole) of spectinomycin and succinic anhydride and 9.1 mg N-hydroxysuccinimide (NHS) were dissolved in 400 mL dimethylformamide (DMF). The reaction mixture was stirred at room temperature for four hours. In a separate tube, 16 mg of dicyclohexylcarbodiimide (DCC) were dissolved in 200 mL DMF and transferred to the succinylate reaction mixture. This reaction mixture was stirred for 1 hour at room temperature and transferred to a refrigerator to continue stirring overnight at 4° C.

Carrier protein KLH (Imject™; Pierce Chemical Co.) was reconstituted in 5.4 mL deionized water (20 mg of protein in phosphate buffered saline, pH 7.2, when reconstituted). Activated hapten was transferred to a microcentrifuge tube and centrifuged for 5 minutes to remove the substituted urea precipitate. Supernatant was transferred to the reconstituted carrier protein solution and stirring was continued for four hours at room temperature. The protein reaction mixture was centrifuged to remove any precipitated protein and the supernatant was applied to a desalting column (Swift™; Pierce Chemical Co.) and eluted with 0.01 M phosphate buffered saline, pH 7.2 in 3-mL fractions. Fractions were monitored at 280 nm and the immunogen typically eluted in fractions 2-4. Fractions containing the immunogen were pooled and lyophilized. The protein conjugation procedure was repeated with bovine serum albumin (BSA, Imject™; Pierce Chemical Co., 20 mg of protein in phosphate buffered saline, pH 7.2 when reconstituted) to prepare coating antigen.

Example 2

Immunization and Antibody Purification

A primary inoculum was prepared from 2.5 mL of the immunogen (1 mg/mL in 0.01 M PBS) and 25 mg *M. tuberculosis* suspension in 2.5 mL of Freund's adjuvant. This suspension was homogenized until thick and creamy. The dose per rabbit was 1.0 mL by subcutaneous injection. Booster inocula were prepared from 1.25 mL of the immunogen (1 mg/mL in 0.01 M PBS) and 1.25 mL of Freund's incomplete adjuvant. This suspension was homogenized until thick and creamy. The dose per rabbit was 0.5 mL by subcutaneous injection every 21 days. Eight days after the first and each subsequent booster injection a test bleed was assayed for antibody titers.

Antisera was assayed in a checkerboard fashion and the titer was taken as the highest dilution of antisera at the highest dilution of coating antigen that gave a response three times the background determined from pre-immunization serum (Voller et al., Bull. World Health Or. 53:35, 1976).

When antibody titers reached an apparent steady state, a production bleed of approximately 20 mL were obtained per rabbit. The antisera was pooled, assayed for protein content and stored frozen (–85° C.) until used. Antibody purification was accomplished by diluting the antisera to 4.6 mg/mL and applying 2-mL aliquots to Protein A affinity columns (AffinityPak™; Pierce Chemical Co.). The column was washed with 15 mL ImmunoPure® IgG Binding Buffer (Pierce Chemical Co.) and eluted with 5 mL ImmunoPure® IgG Elution Buffer (Pierce Chemical Co.) in 1-mL fractions. The absorbance of each fraction at 280 nm was monitored and the fraction with significant absorbance (usually fraction #2) was desalted with a 5-mL Excellulose™ column (Pierce Chemical Co.) which had previously been conditioned with 10 mL of 0.02 M PBS (100 mM NaCl, pH 7.4). Elution was in 1-mL fractions and the absorbance was monitored at 280 nm. Fractions containing significant absorbance (usually fractions 3-4) where pooled and assayed for total protein.

Example 3

Description of the Test Protocol

The following method is a competitive enzyme linked immunosorbent assay (ELISA) for the assay of spectinomycin residues in various animal tissues and fluids and is applicable to total residue concentrations of approximately 0.1 ppm to in excess of 200 ppm in tissues.

Tissue Extraction Procedure:

A five-gram aliquot of tissue was weighed into a 250-mL centrifuge bottle. After the addition of 50 mL PBST extraction buffer (0.1% Tween-20 in 0.01 M phosphate buffered saline, pH 7.2), sample was homogenized using a Polytron homogenizer. The homogenized sample was centrifuged at 5,000 g-av for 30 minutes at 10° C. to sediment the solids. Supernatant was decanted into a 250-mL graduated cylinder. The homogenization and sedimentation process was repeated two more times, the supernatants were combined and the final volume adjusted to 200 mL with extraction buffer.

To the combined supernatants, 1 mL of 4% sodium azide was added (final concentration 0.02%) to prevent microbial growth. The entire sample was further clarified by centrifugation and the supernatant was carefully decanted. A 4-mL aliquot of extract processed in this manner corresponds to 0.1 g of tissue.

Plate Plan:

A plate plan was laid out for each microtiter plate prior to the start of the assay. The plate plan designates wells for standard curves, antigen-negative wells, primary antibody negative wells, a positive control well and samples with replicates.

Coating Antigen:

The coating antigen (100 µL) was added to each well according to the plate plan. Wells were selected as antigen-negative are coated with 0.01 M PBS only. Plates were covered with sealing tape and lids, and sealed plates were incubated overnight at 4° C. A positive control will contain antibody instead of coating antigen.

Wash Procedure:

The plates coated with coating antigen were removed from the refrigerator and were washed in three consecutive addition/aspiration steps with washing buffer (0.01% Tween-20 in 0.01 M PBS). A washer/aspirator designed for washing 96-well microtiter plates (Handiwash; Dynatech Laboratories, Inc. or equivalent) was utilized.

After the third addition of washing buffer, wells were incubated with washing buffer at room temperature for approximately 3–5 minutes. The plate was then washed in two additional consecutive addition/aspiration steps. Excess washing buffer was aspirated from the wells and the plate was inverted and tapped dry on a paper towel or other absorbent surface.

Blocking Procedure:

All wells of the microtiter plate had 300 µL of Blocking Solution (1% BSA in 0.01 M PBS) added to each well. The plates were incubated at room temperature for one hour or overnight at 4° C.

Wash:

The washing procedure described above is repeated to remove excess BSA. The coated, blocked and washed plates were either used immediately or sealed with sealing tape and stored refrigerated (4° C.) for up to 3 days or frozen (−20° C.) for up to one month.

Sample Spiking Procedure:

Ninety six low protein binding micro-tubes were arranged in a tube rack with an 8×12 array to correspond to the microtiter plate plan. Duplicate external standard curves were established. Remaining tubes contained up to seven replicates of the diluted tissue extracts to which was added 190 µL of diluted sample and 10 µL of the protein A purified antibody (pAIgG). Positive control tubes contained 200 µL PBST. To the antibody negative controls, 10 µL of 0.01 M PBS buffer were added instead of pAIgG. All tubes were vortexed after the antibody addition, incubated for approximately one hour and 100 µL transferred from each tube to the corresponding well in the microtiter plate according to the plate plan. Plates were incubated for one hour at 37° C. or overnight at 4° C.

Microtiter Plate Assay Procedure:

After incubation, plates were removed from the refrigerator and washed with washing buffer as described.

Addition of Secondary Antibody:

To each well 100 µL of the 1:5000 dilution of secondary antibody, goat, anti-rabbit IgG conjugated to alkaline phosphatase (Pierce Chemical Co.) was added and the plates were covered with a lid and incubated for one hour.

Wash:

After incubation, unbound secondary antibody was removed by the washing procedure as described.

Addition of Enzyme Substrate and Absorbance Measurements:

To each well, 100 µL of the substrate (para-nitrophenyl phosphate or PNPP; Pierce Chemical Co.) was added. Plates were covered with a lid and incubated at room temperature. Color development was typically noted in the positive control well within 15 minutes. Initial readings were taken after one hour, 90 minute and 2 hour incubation periods, if necessary.

Readings were taken using a microtiter plate reader at 410 nm. Antibody negative control wells were background subtracted from the remaining wells. Incubation was carried out long enough to give absorbance in the standard curve wells that was in the range of 0.3–0.5 Absorbance Units when no antigen was present.

Example 4

Assay of Analyte Residues in Bovine Liver and Kidney Tissue

To assess accuracy of the method, liver and kidney tissue samples from cattle with incurred $^3$H-spectinomycin residues were extracted in the manner described in Example 3.

Accuracy of the method was shown by the overall average tissue residue concentration measured from incurred [$^3$H]-spectinomycin in tissue extracts at both the ppm level and ppb level. The accuracy ranged from 76% to 109% with an average (n=21) of 95% when the analyses were performed by an experienced analyst. These results are presented below in Table 1.

TABLE 1

Measurement of Incurred [$^3$H]-Spectinomycin Residues

| Withdrawal Interval | Tissue | Actual Incurred Residues, ppm | Average Measured Residues, ppm | Percent Accuracy |
|---|---|---|---|---|
| Day 0 | Liver | 93.7 | 97 | 103 |
|  | Kidney | 232.2 | 224 | 96 |
| Day 3 | Liver | 43 | 36 | 85 |
|  | Kidney | 90.8 | 99 | 109 |
| Day 7F | Liver | 20.9 | 20 | 96 |
|  | Kidney | 10.1 | 7.7 | 76 |
| Day 21 | Liver | 2.5 | 2.5 | 100 |

The accuracy of triplicate measurements of tissues with incurred residues by a newly trained analyst ranged from 71% to 122% with an average (n=18) of 93% over the range of tissues analyzed. These results are presented in Table 2.

TABLE 2

Measurement of Incurred [$^3$H]-Spectinomycin Residues

| Withdrawal Interval | Tissue | Actual Incurred Residues, ppm | Average Measured Residues, ppm | Percent Accuracy |
|---|---|---|---|---|
| Day 0 | Liver | 93.7 | 86 | 91 |
| Day 3 | Liver | 43 | 53 | 122 |
| Day 7M | Kidney | 36.6 | 39 | 106 |
| Day 7F | Liver | 20.9 | 19 | 91 |
| Day 14 | Liver | 4.9 | 3.5 | 71 |

Figure 3:
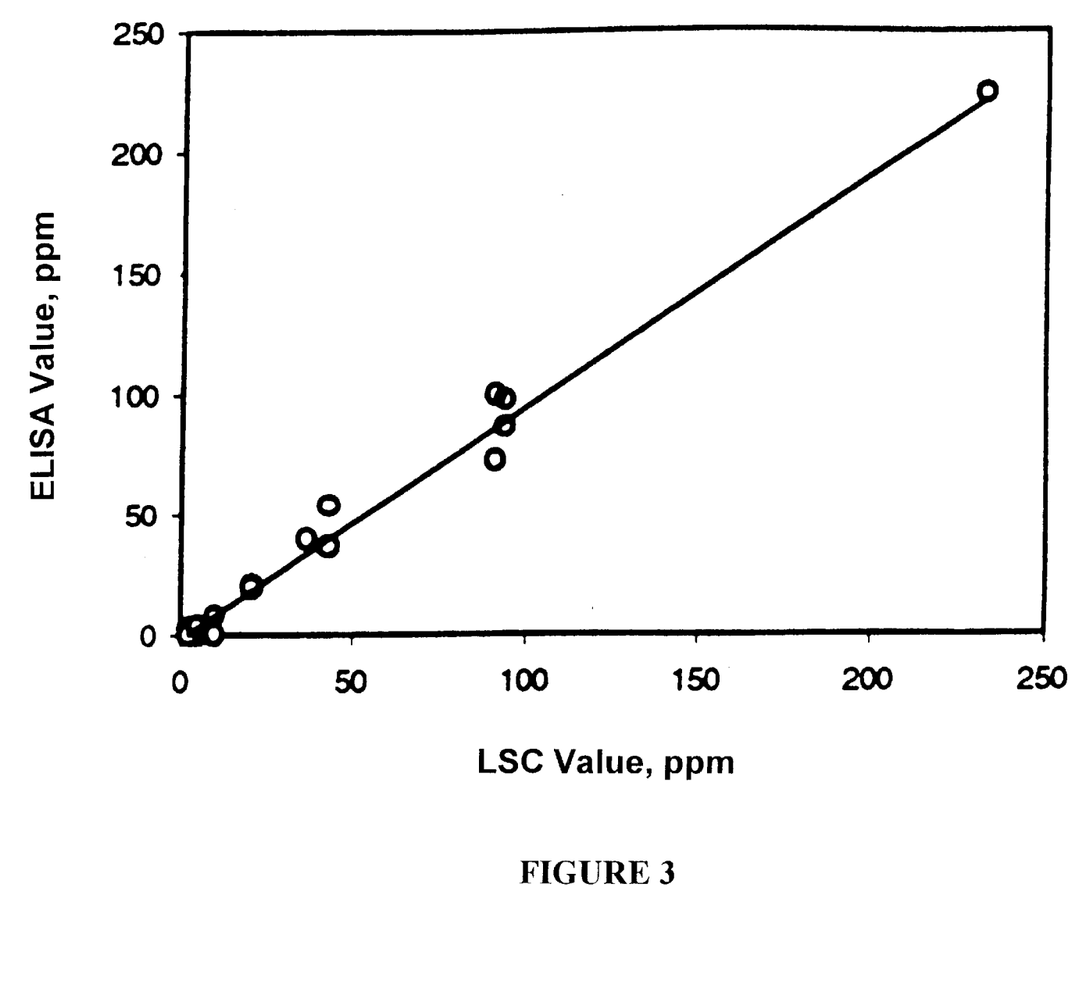
FIG. 3  Correlation of total spectinomycin related residues from bovine liver and kidney tissues as measured by ELISA and radiotracer analysis.

Equivalency of the ELISA method as compared to standard isotopic methods for total residue analysis is demonstrated in FIG. 3. Correlation ($R^2$=0.995) between total spectinomycin related residues from bovine liver and kidney tissues measured by ELISA and radiotracer (LSC) analysis. Results are from data collected on different analysis days by an experienced analyst (n=21) and a newly trained analyst (n=18).

Example 5

Assay of Analyte from Fortified Tissue

To assess precision of the method, liver tissue homogenates were fortified at concentrations of 0.5, 1.0 and 2.0 ppm and were assayed by the ELISA method described in Example 3 on three non-consecutive days by a single analyst. Percent recovery was calculated from the average of five replicate analyses at each fortification level on each analysis day and ranged from 85–98% while the precision (Percent CV) within the assays ranged from 2% to 22% and the precision between the analysis days ranged from 6% to 11% with an overall precision of 7%. These results are tabulated in Table 3.

TABLE 3

Precision and Accuracy Measurement from Fortified Tissue

| Sample | Tissue Concentration ($\mu$g/mL) | | |
|---|---|---|---|
|  | 0.5 | 1 | 2 |
| Day 1 | 0.47 ± 0.01 | 0.95 ± 0.07 | 1.44 ± 0.32 |
| Day 3 | 0.46 ± 0.01 | 0.78 ± 0.09 | 1.82 ± 0.09 |

TABLE 3-continued

Precision and Accuracy Measurement from Fortified Tissue

| Sample | Tissue Concentration ($\mu$g/mL) | | |
|---|---|---|---|
|  | 0.5 | 1 | 2 |
| Day 13 | 0.53 ± 0.02 | 0.92 ± 0.05 | 1.83 ± 0.09 |
| N | 15 | 15 | 15 |
| Avg Conc. ($\mu$g/mL) | 0.49 | 0.88 | 1.7 |
| % Precision$_{within\ assay}$ | 2 | 8 | 11 |
| % Precision$_{between\ assays}$ | 6 | 8 | 11 |
| % Recovery | 98 | 88 | 85 |

Example 6

Competitive Assay Using Immobilized Antibody

Antibody was immobilized and antigen conjugated to an enzyme (horseradish peroxidase) for use in the competitive assay. Briefly, sample was added directly to microtiter plates and incubated 1 hour at 37° C. or overnight at 4° C. After washing to remove unbound antigen, antigen-enzyme conjugate was added and the plates were incubated and washed to remove unbound antigen-enzyme complex. Substrate (o-phenylenediamine or tetramethylbenzidine) was added and a color developed. Absorbance was measured either fluorimetrically or spectrophotometrically respectively and was inversely proportional to the spectinomycin related residue concentration in the sample.

Example 7

Competitive Assay using Immobilized Hapten

Antibody was conjugated to an enzyme (horseradish peroxidase) and incubated with the sample containing spectinomycin-related residues. After incubation, an aliquot was added to the wells of a microtiter plate containing immobilized antigen. After a second incubation, and washing to remove unbound antibody, enzyme substrate was added. Color or fluorescence was inversely proportional to the concentration of spectinomycin related residues.

Alternative assay methods include labeling the antibody or antigen directly with a color or fluorescent dye molecule, a color or fluorescent dye particle or a magnetic particle. In these assays no substrate is required and the result can be read directly without additional incubation and sometimes without aid of a spectrophotometer or other instrumentation. In another alternative, the microtiter plate can be replaced with nitrocellulose or other absorbent filter membrane. In this alternative, antigen or antibody are first absorbed to the membrane, and the assay is conducted as described in the previous embodiments. Results can be visualized either on the membrane surface or in the filtrate passing through the membrane.

Other embodiments and uses of the invention will be apparent to those skilled in the art from consideration of the specification and practice of the invention disclosed herein. All U.S. patents and other documents cited herein are specifically incorporated by reference. It is intended that the specification and examples be considered exemplary only, with the true scope and spirit of the invention being indicated by the following claims.

I claim:

1. An immunogen formed by a process comprising: adding an organic compound having a plurality of functional groups, said plurality of functional groups including at least one amine functional group and at least one hydroxyl group, to a homobifunctional carboxylic cross-linking agent in the presence of a hydroxylimide catalyst to form an adduct with a free carboxyl moiety; activating the free carboxyl moiety of the adduct with a carbodiimide and eliminating a urea group to form an activated ester; and conjugating the active ester to an immunogenic carrier containing a primary amine to form the immunogen containing an amide bond between a spacer arm and the organic compound.

2. The immunogen of claim 1 wherein adding, activating or conjugating is carried out in a polar, aprotic organic solvent.

3. The immunogen of claim 2 wherein the solvent is dimethylformamide, dioxane, dimethyl sulfoxide or acetonitrile.

4. The immunogen of claim 1 wherein the organic compound is spectinomycin or dihydrospectinomycin.

5. The immunogen of claim 1 wherein the homobifunctional carboxylic cross-linking agent is succinic anhydride.

6. The immunogen of claim 1 wherein the catalyst is N-hydroxysuccinimide.

7. The immunogen of claim 1 wherein the carbodiimide is dicyclohexylcarbodiimide.

8. The immunogen of claim 1 wherein the active ester is the N-hydroxysuccinyl ester.

9. The immunogen of claim 1 which comprises a protein containing free amine functional groups or a protein in which free amine functional groups have been introduced through chemical modification.

10. The immunogen of claim 1 wherein the immunogenic carrier is selected from the group consisting of bovine serum albumin, ovalbumin keyhole limpet hemocyanin and a polysaccharide modified to introduce free amine functional groups.

11. The immunogen of claim 10 wherein the polysaccharide is dextran, sepharose, agarose or cellulose.

12. The immunogen of claim 1 wherein the immunogenic carrier is a synthetic polymer or copolymer comprising polyacrolein or polyacrylamide or polyamide or polybutyrate or polyurea or polyureamide or polystyrene wherein a free amine is present or introduced as a result of modification.

13. The immunogen of claim 1 wherein the organic compound is selected from the group consisting of spectinomycin, dihydrospectinomycin, penicillin, erythromycin and chloramphenicol.

14. A kit for the detection of organic compounds comprising the immunogen of claim 1 coupled to a solid support.

* * * * *